(12) United States Patent
Berler et al.

(10) Patent No.: US 10,732,164 B2
(45) Date of Patent: Aug. 4, 2020

(54) SYSTEM AND METHOD FOR HEADSPACE MONITORING IN TRANSFORMERS

(71) Applicant: ZTZ Service International, Inc., North Miami Beach, FL (US)

(72) Inventors: Zalya Berler, Sunny Isles Beach, FL (US); Vladimir Prykhodko, Sunny Isles Beach, FL (US); Aleksey Smirnov, Sunny Isles Beach, FL (US); Vasily Topko, Tamarac, FL (US)

(73) Assignee: ZTZ Service International, Inc., North Miami Beach, FL (US)

( * ) Notice: Subject to any disclaimer, the term of this patent is extended or adjusted under 35 U.S.C. 154(b) by 0 days.

(21) Appl. No.: 16/217,646

(22) Filed: Dec. 12, 2018

(65) Prior Publication Data
US 2020/0191763 A1  Jun. 18, 2020

(51) Int. Cl.
*G01R 31/62* (2020.01)
*G01N 33/28* (2006.01)
*G08B 21/18* (2006.01)

(52) U.S. Cl.
CPC ......... *G01N 33/2841* (2013.01); *G01R 31/62* (2020.01); *G08B 21/182* (2013.01)

(58) Field of Classification Search
CPC ........ G01R 31/02; G01R 31/14; G06N 7/005; H01F 27/12
See application file for complete search history.

(56) References Cited

U.S. PATENT DOCUMENTS

| | | | | |
|---|---|---|---|---|
| 3,504,319 | A * | 3/1970 | Leonard | H01F 27/266 336/68 |
| 6,446,027 | B1 * | 9/2002 | O'Keeffe | G01R 31/02 702/183 |
| 7,928,329 | B2 * | 4/2011 | Findeisen | H01H 9/0044 174/8 |
| 8,028,561 | B2 | 10/2011 | Herz et al. | |
| 8,511,160 | B2 | 8/2013 | Herz et al. | |
| 8,839,658 | B2 | 9/2014 | Herz et al. | |
| 9,018,962 | B2 | 4/2015 | Hoffman et al. | |
| 9,977,006 | B2 | 5/2018 | Park et al. | |
| 1,012,634 | A1 | 11/2018 | Berler et al. | |
| 2013/0285671 | A1 | 10/2013 | Hoffman | |
| 2014/0163911 | A1 | 6/2014 | Rohrer | |
| 2014/0368215 | A1 | 12/2014 | Hoffman | |
| 2016/0322151 | A1 * | 11/2016 | Larsson | H01F 27/40 |

* cited by examiner

*Primary Examiner* — Douglas X Rodriguez
*Assistant Examiner* — Brent J Andrews
(74) *Attorney, Agent, or Firm* — Pablo Meles

(57) ABSTRACT

A sensor module or system for monitoring a headspace of a transformer can include a sealed chamber configured for coupling and accessing gasses from the headspace of the transformer, a plurality of sensors placed within the sealed chamber which can include a hydrogen sensor and at least a second sensor such as a total combustible gas sensor, a moisture sensor, a pressure sensor, or a temperature sensor. The module or system can include one or more processors coupled to the plurality of sensors where the processors are configured to generate an alarm signal when a combination of the hydrogen sensor and at least the second sensor exceed a predetermined threshold.

20 Claims, 7 Drawing Sheets

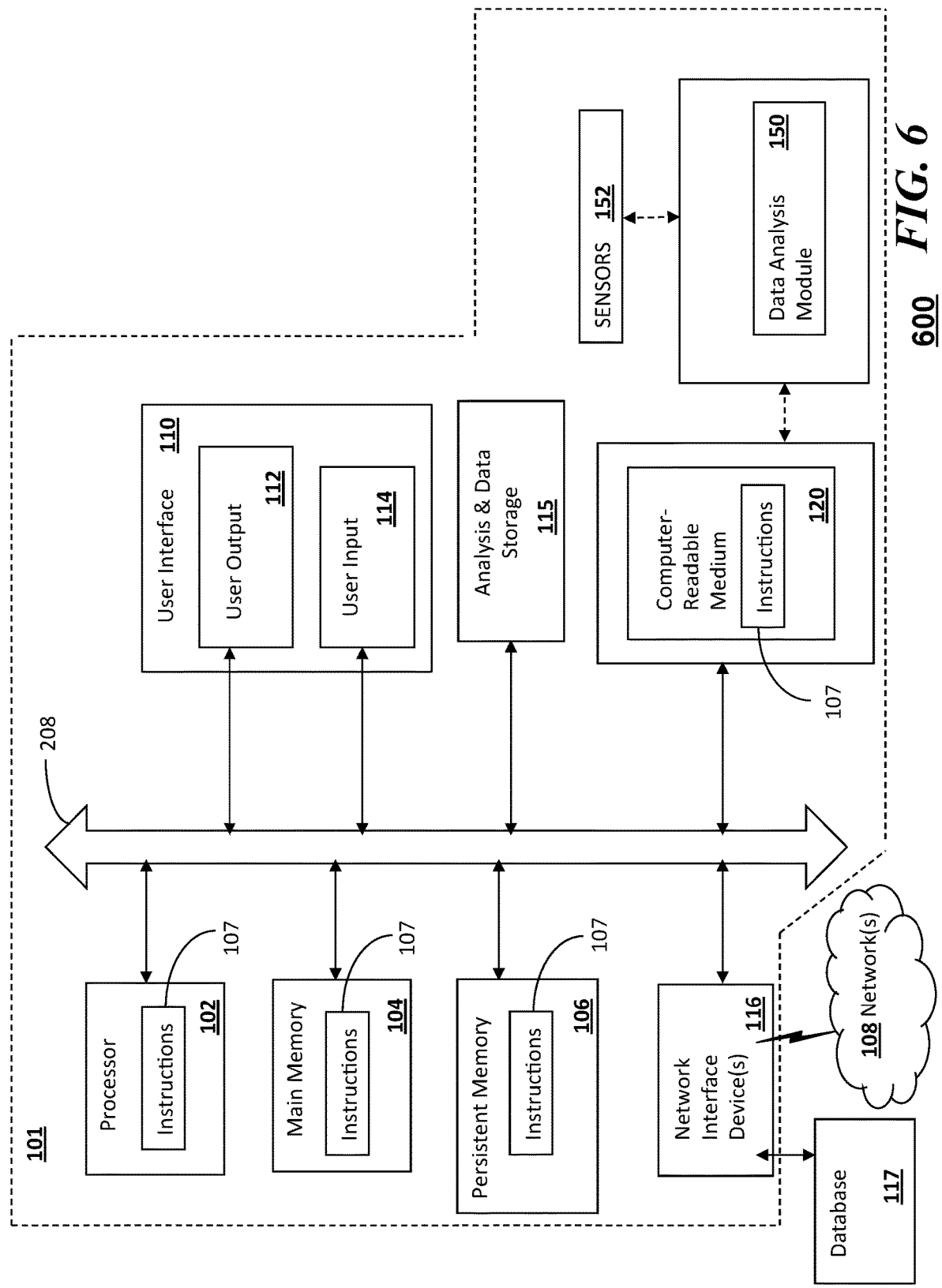

SYSTEM AND METHOD FOR HEADSPACE MONITORING IN TRANSFORMERS

FIELD OF THE DISCLOSURE

The present disclosure generally relates to systems and methods for monitoring the performance of transformers. In particular, the systems and methods can detect the occurrence of faults in the insulation or oil of such transformers and provide signals that trigger indications or alarms indicative of such faults.

BACKGROUND

High voltage generator and transmission transformers form an integral part of any electrical power generation distribution and transmission system and are subject to degradation over time or due to environmental factors that impact the insulation which typically includes oil. Oil filled transformers can include paper which is wound around the copper windings. There are spacers, washers, seals, lead through plates, taps and bushings, which are also part of the insulation system within the transformer. In order to enhance the insulation and stability, the paper is permeated with a dielectric, typically mineral oil or silicone oil, which fills the transformer. This insulating oil also serves as a coolant, distributing heat by convection or forced flow, and also quenches discharges. Other types of transformers include high frequency communication transformers which use solid polymeric dielectrics such as epoxy thermoset, which is vacuum back-filled into the transformer, and gas-filled transformers.

The operating lifetime of a high voltage transformer can be greater than 35 years. The lifetime depends on the loading, design, quality of manufacture, and materials and maintenance routines. During its lifetime, the transformer insulation can degrade, the rate of degradation being dependent upon the workload and the internal operating environment of the transformer, such as temperature, moisture content, pH and the like. Any degradation of the insulation, such as electronic and ionic plasma erosion of solid insulation surrounding an air bubble occluded due to faulty manufacture, can result in increasing levels of partial discharge within the transformer. Occurrence of partial discharges also leads to evolution of gases such as hydrogen and acetylene within the transformer. Such increased partial discharge leads to further degradation of the insulation which in turn leads to increasable levels of partial discharge. Continued degradation of the insulation can result in severe discharges, short-circuit faults or a catastrophic failure due to an explosion of the gases, for example, hydrogen, acetylene and ethylene, produced as chemical by-products of the degradation process. Such failure can result in reduction or loss of supply to the power system, incur considerable expense for the replacement or repair of the transformer and also present a serious risk to nearby personnel and the environment.

Partial discharge in transformers can also occur due to faulty manufacture and/or mechanical or electrical fatigue. For example, the movement of loose components, and creep and stress relaxation of metallic components, such as fastenings, or foreign metallic bodies within the transformer, provide an opportunity for discharges to occur even when there has been no or little degradation of the insulation.

Partial discharge in transformers can also arise due to windings becoming loose within the transformer. Wear and tear suffered by the tap connectors in the tap changer can also cause partial discharges. Faults in the bushings can also result in partial discharges.

It is known that a partial discharge can produce signals at different locations within a large transformer including a discharge current in neutral caused by imbalance, a displacement current through the capacitive tapping of a bushing, a radiated radio frequency (RF) pulse or wave and a radiated ultrasonic (US) pulse or wave.

The magnitude of partial discharge within a transformer provides one means of determining the integrity of the transformer's insulation. For example, a detected partial discharge having a magnitude of 50 pC would normally be ignored at normal voltage operations, a reading of 500 pC would be viewed with some concern, while a reading of 5000 pC would be considered potentially dangerous.

Power authorities typically test transformers by sampling the mineral oil within the transformer about once a year to determine the oil's dissolved gas concentration by analysis (DGA) and dielectric loss angle (DLA). If high gas readings are obtained, the frequency of sampling is increased to monthly and even weekly. However, there is always some delay between the sampling and the analysis in the laboratory. Rapid deterioration of insulation may not be detected and transformers have failed catastrophically even when DGA sampling has been carried out. Since it is known that partial discharges of a higher magnitude and/or repetition rate develop shortly before a major failure, continuous monitoring of electrical equipment, while it is kept on-line, to provide early warning, is very desirable.

Partial discharge can be measured using instruments such as Robinson, Haefly or Tettex partial discharge detectors, which detect high frequency electrical (RF) signals only, by coupling to the lower part of the bushing on the transformer or to the windings using capacitor dividers and a toroid system. These instruments are normally used in a test bay during high voltage proving tests for a new or re-wound transformer. These measurements can, however, normally not be undertaken in a substation location due to the high level of electrical interference. Making reliable readings with these instruments also requires considerable skill.

BRIEF DESCRIPTION OF DRAWINGS

FIG. 6 is a block diagram illustrating s system in accordance with an embodiment.

DETAILED DESCRIPTION

In accordance with one or more embodiments, a system herein is designed for monitoring the technical state of a transformer such as a power transformer using various methods that can include, the detection or measure of hydrogen in the headspace of a gas tank or as a component or dissolved from the oil-based insulation of the transformer and the further detection of another parameter indicative of transformer degradation such as the detection of total combustible gases in the tank, detection (and control) of moisture content in oil-based insulation of the power transformer, detection of the temperature of the transformer tank, detection of pressure, and/or detection of the presence of partial discharges inside the tank. In one embodiment, such measurements can be made via a combination sensor that samples oil from a transformer tank via a drain valve towards the bottom of a tank. Such an embodiment, when used with a submersible power transformer tank (which can be buried underground) may provide difficulty providing access to the drain valve and corresponding sensors. Retrofitting existing submersed power transformers, or accessing or replacing of such sensors towards the bottom of the power transformer tank in such scenarios can be cumbersome since it can involve extensive digging to retrofit, access, or replace such sensors. Note that the following description of the embodiments may use the same reference numbers among the different embodiments to refer to the same or similar components shared by the various embodiments.

Figure 1:
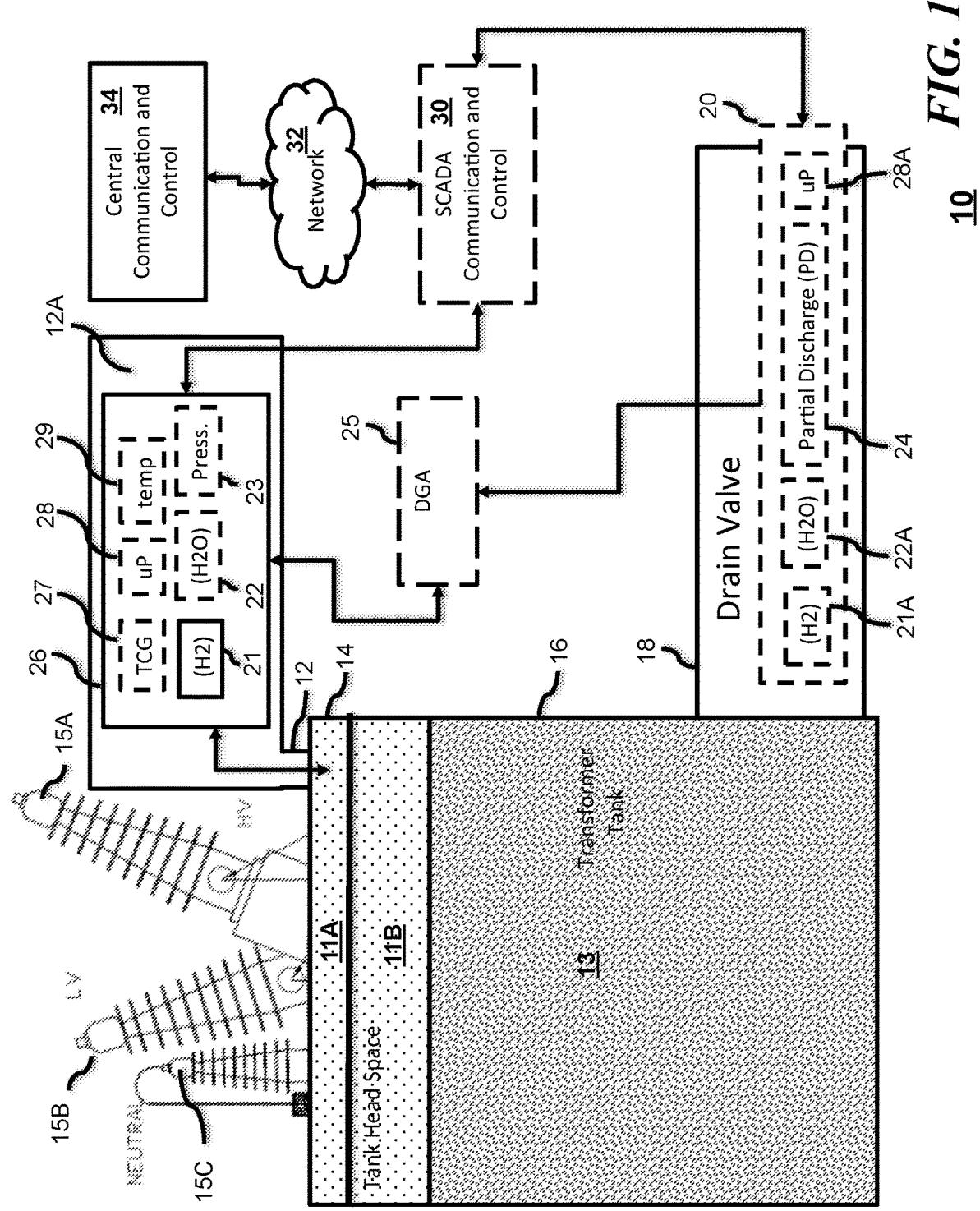
FIG. 1 is a block diagram of a monitoring system in accordance with an embodiment.
Figure 3:
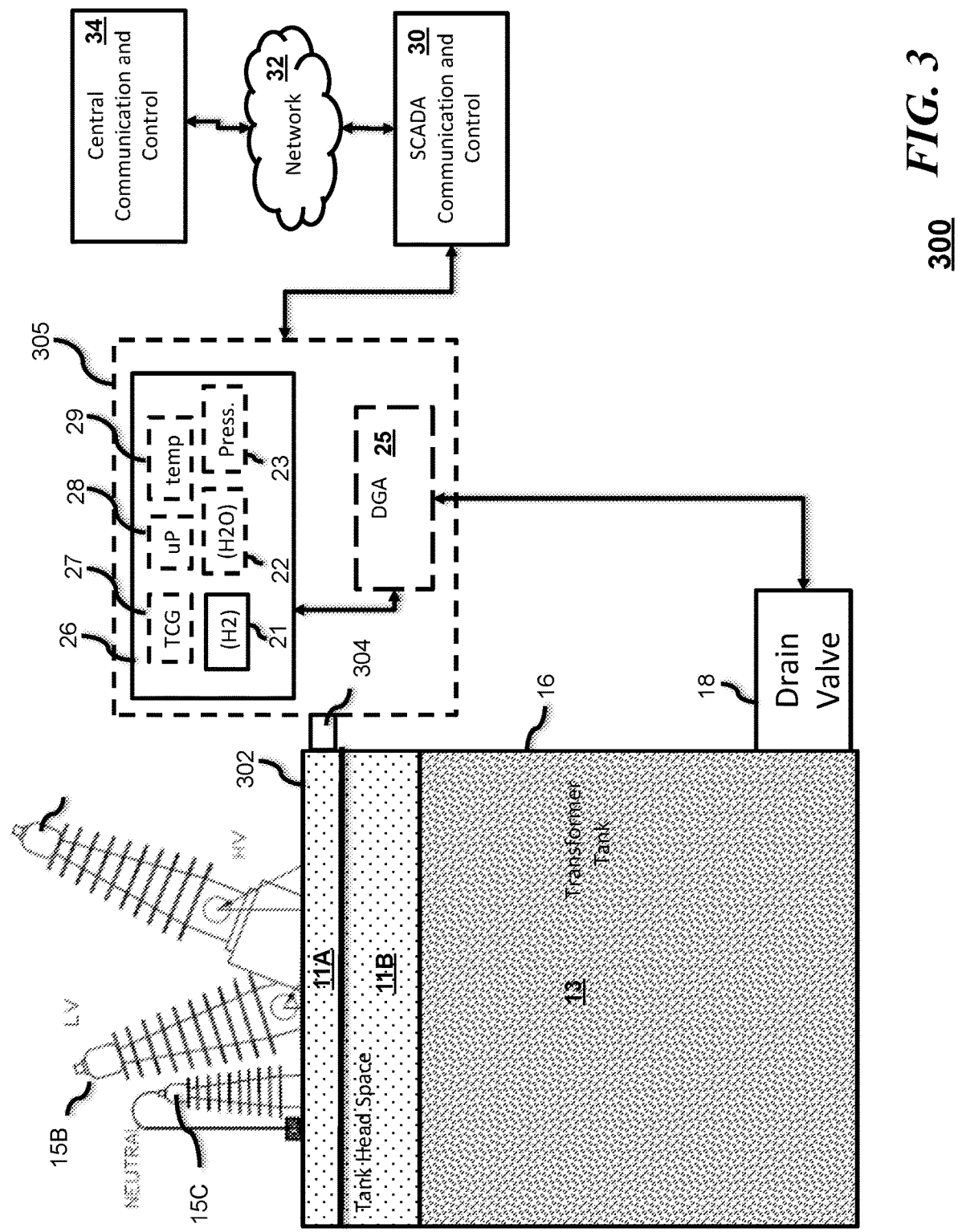
FIG. 3 is another block diagram of a monitoring system in accordance with an embodiment.
Figure 4:
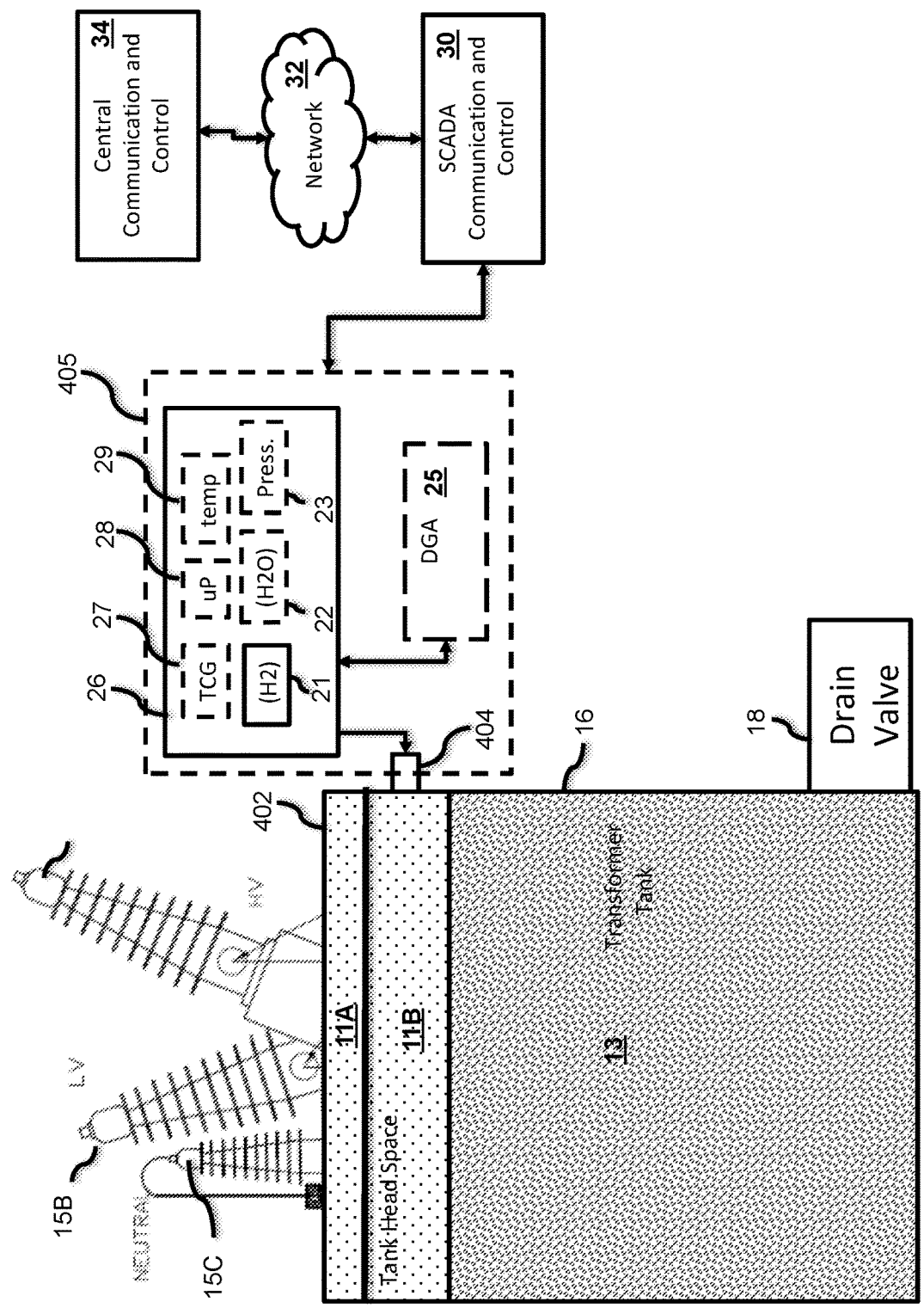
FIG. 4 is another block diagram of a monitoring system in accordance with an embodiment.

A system 10 in accordance with some of the embodiments illustrated in FIG. 1 can include a power transformer tank 16 containing some form of insulation material 13 such as mineral oil and a cap 14 that seals the contents of the power transformer tank 16 and forms a tank headspace 11A and 11B above the insulation material 13 within the tank 16. The headspace 11A is the area of gas formed within the volume of the cap and the headspace 11B is the area of gas formed within the volume of the top of the tank exclusive of the volume of the cap. The volume of area of 11A and 11B can be one contiguous area. The system 10 can further include a high voltage bushing 15A, a low voltage bushing 15B, and a neutral bushing 15C. The system 10 can further include a drain valve 18 that enables access to the insulation material 13 such as oil. Optionally, a combination sensor 20 can include sensors 21A for measuring hydrogen (H2), sensors 22A for meauring moisture (H2O), sensors 24 for measuring partial discharge, and optionally a microprocessor 28A coupled to such sensors. The combination sensor 20 can be used in combination with other sensors in accordance with the embodiments and in some instances may already be installed in a pre-existing system. The system 10 can further include communication equipment or telemetry to relay or transmit data to a central communications and control module 34. Such communication equipment can include a SCADA communication and control module 30 and a network 32 coupling to the module 34. Other communication systems such as cellular, WiFi or other wireless or even wired networks may be used as a suitable alternatives. The sensor 20 can also communicate with a dissolved gas analyzer 25. To provide greater access and ease of access to additional information or even similar information, the system 10 can include in some embodiments a sensor module 12 coupled with or alternatively formed in the power transformer cap 14 or elsewhere on the transformer tank that has access to the tank headspace 11A or 11B. The sensor module 12 can have a sealed chamber 12A having any number of sensors such as gas sensors made by SGX Sensorthech or other suitable manufacturers. In the embodiment shown in FIG. 1, the sensor module 12 is formed on the top portion of the power transformer cap 14, but the sensor module can be placed or formed elsewhere as shown in FIGS. 3 and 4. The sensor module 12 can be coupled to another sensor 26 that measures or analyzes other parameters. The sensor 26 can include at least a hydrogen or H2 sensor 21 and at least one or more other sensors. Such other sensors can include a moisture or H2O sensor, a pressure sensor 23, a temperature sensor 29, and a total combustible gas or TCG analyzer or sensor 27 that can analyze or measure gases. The sensor 26 can further include a processor 28. The sensor 26 can optionally be coupled to the dissolved gas analyzer 25 which does not necessarily reside within the sealed chamber 12A of sensor module 12 (as shown in FIG. 1). The information gathered or analyzed by sensor 26 can also be communicated to the central communication and control module 34 via a communication system or network such as the SCADA communication and control module 30 and via the network 34.

Figure 1A:
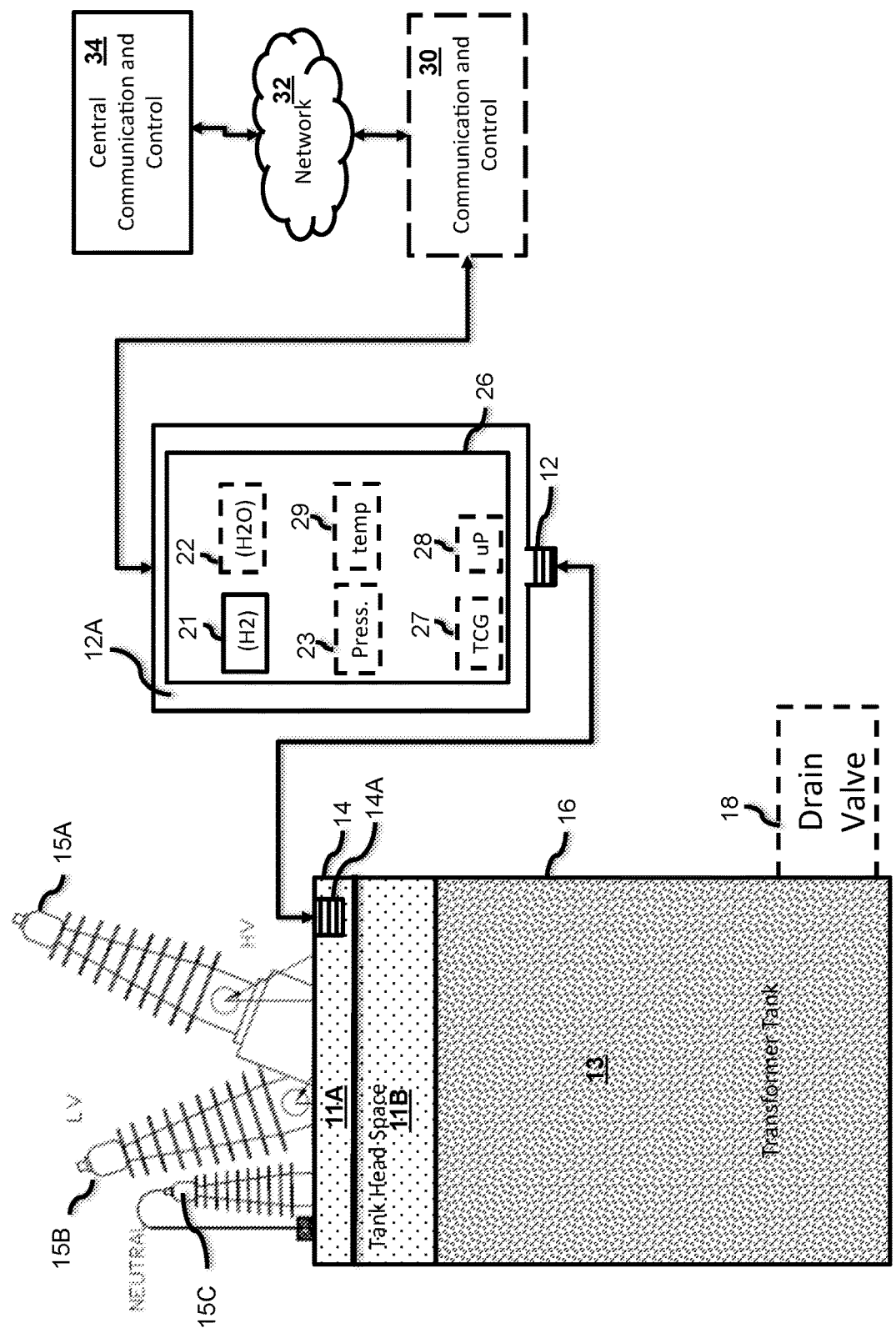
FIG. 1A is a block diagram of a variation of the monitoring system of FIG. 1 in accordance with an embodiment.

A system 10A in accordance with some of the embodiments illustrated in FIG. 1A is a more simplified version of the system 10 of FIG. 1 and can include the power transformer tank 16 containing the insulation material 13 and the cap 14 that seals the contents of the power transformer tank 16 and forms a tank headspace 11A and 11B above the insulation material 13 within the tank 16. The headspace 11A is the area of gas formed within the volume of the cap and the headspace 11B is the area of gas formed within the volume of the top of the tank exclusive of the volume of the cap. The volume of area of 11A and 11B can be one contiguous area. The system 10 can further include the bushings 15A, 15B, and 15C. The system 10 can optionally include the drain valve 18. The system 10A can further include communication equipment or telemetry to relay or transmit data to a central communications and control module 34. Such communication equipment can include a communication and control module 30 and a network 32 coupling to the module 34. Other communication systems such as cellular, WiFi or other wireless or even wired networks may be used as a suitable alternatives.

The system 10A can include in some embodiments a sensor module 12 configured to coupled with the power transformer cap 14 or elsewhere on the transformer tank that has access to the tank headspace 11A or 11B. In one embodiment, the sensor module 12 can be coupled to the transformer tank by screwing an access point of the sealed chamber 12A into an access point in the transfer tank 16 at 14A. For example, the sensor module can have a threaded potion that mates with the threaded portion 14A of the transformer tank 16. The mating can include gaskets and other appropriate features to provide a leak proof mating. As previously explained above with respect to FIG. 1, the sensor module 12 can have a sealed chamber 12A having any number of sensors such as gas sensors made by SGX Sensorthech or other suitable manufacturers. In the embodiment shown in FIG. 1A, the sensor module 12 is mated or coupled on the top portion of the power transformer cap 14, but the sensor module can be coupled elsewhere depending on the access points provided or created on the transformer tank. The sensor module 12 can be coupled or be part of another sensor 26 that measures or analyzes other parameters. The sensor 26 can include at least the hydrogen or H2 sensor 21 and at least one or more other sensors such as the moisture or H2O sensor 22, the pressure sensor 23, the temperature sensor 29, and a total combustible gas or TCG analyzer or sensor 27 that can analyze or measure different gases. The sensor 26 can further include a processor, programmable logic unit, or microprocessor 28. The information gathered or analyzed by sensor module or sensor 12 or 26 can also be communicated to the central communication and control module 34 via a communication system or network such as the communication and control module 30 and via the network 34.

Figure 2:
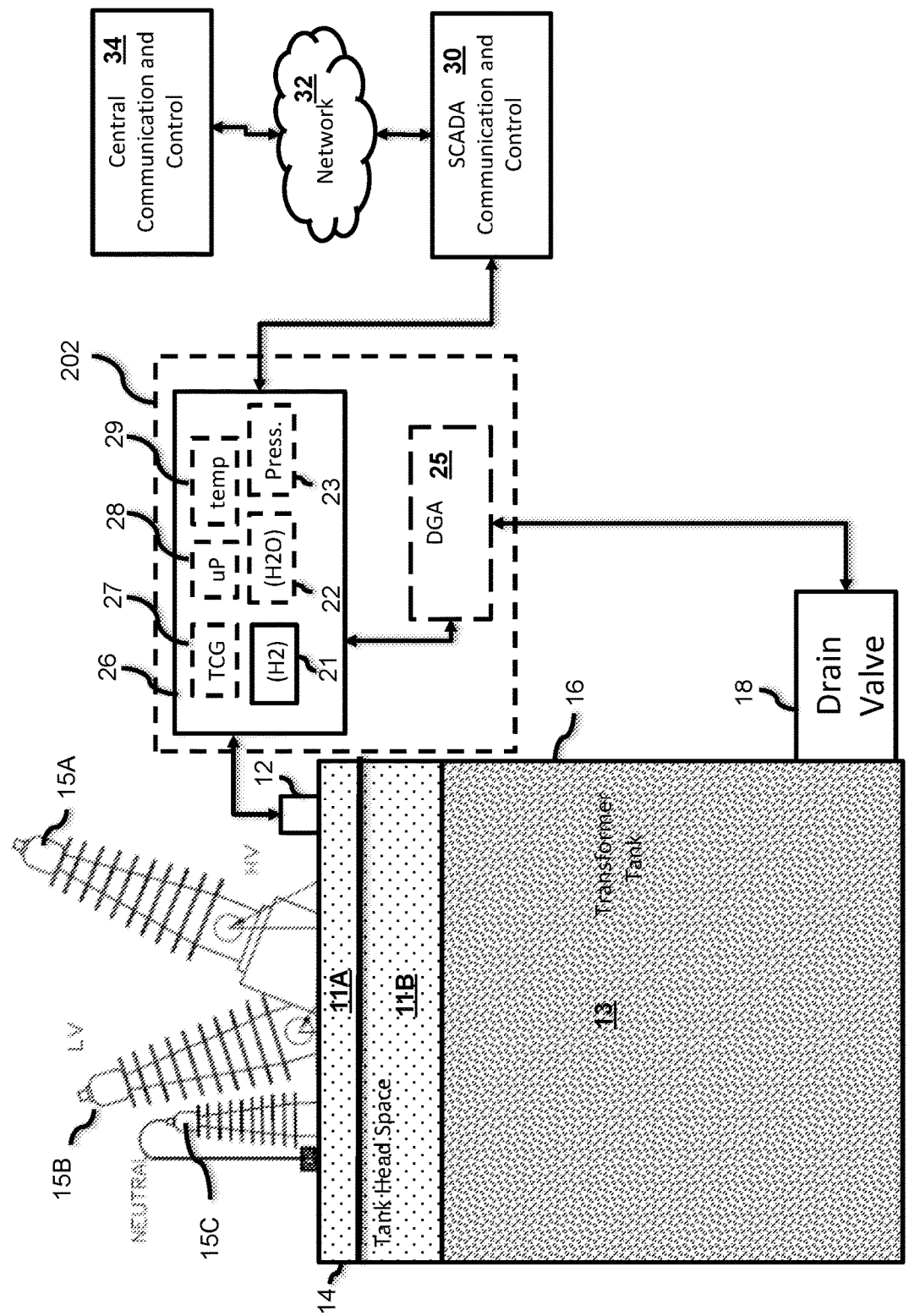
FIG. 2 is a block diagram of another monitoring system in accordance with an embodiment.

In other embodiments as illustrated in FIGS. 2, 3 and 4, such measurements can be made from at least one or more sensors in a cap of a power transformer tank or at least a sensor that accesses the tank headspace where gases reside within a sealed tank rather than further relying on sensors that need access to the drain valve 18. In one embodiment as illustrated in the system 200 of FIG. 2, the sensor module 12 can be coupled to or formed on the upper portion of the power transformer tank corresponding to the location where gases are retained in the headspace of the transformer tank and more particularly on the top portion of the cap 14 of power transformer tank. The sensor module 12 can be part of a combination sensor module 202 that resides within a sealed chamber of the sensor module 12 that includes at least a sensor 26 that includes at least the hydrogen sensor 21 and at least one or more other sensors that monitors and provides an indication of possible degradation of the insulation material 13 within the tank 16. The one or more other sensors can include one or more among the moisture sensor 22, the pressure sensor 23, the temperature sensor 29, and/or the total combustible gas sensor 27. The sensor module 12 or 202 can include the microprocessor 28 and optionally a dissolved gas analyzer 25 as illustrated. The dissolved gas analyzer (DGA) would need likely need access to the drain valve 18 unless the DGA can suitable utilize and analyze the gases from the headspace 11A and 11B. As with other embodiments, the information gathered or analyzed by sensor 12, 202, 26, and/or 25 can also be communicated to the central communication and control module 34 via the SCADA communication and control module 30 and via the network 34 or other suitable communications network.

In yet another embodiment and referring to a system 300 of FIG. 3 similar to the system 200 of FIG. 2, at least one or more sensor module 304 in a side or peripheal portion of a cap 302 of a power transformer tank accesses the tank headspace (11 and 11A) where gases reside within a sealed tank. The sensor module 304 can include a combination sensor module 305 or part of the sensor 26 having at least a hydrogen sensor 21 and at least one or more additional sensors such as the moisture sensor 22, the pressure sensor 23, the temperature sensor 29, and the total combustible gas sensor 27. The sensor can further include microprocessor 28 and optionally a dissolved gas analyzer 25 as illustrated coupled to access the transformer tank 16 via the drain valve 18. For clarity, none of the embodiments in FIG. 1, 2 or 3 require the DGA 25 and it is only illustrated as an optional feature.

The sensor module 304 can communicate data with and among the components of the the combination sensor module 305 or the sensor 26 in a wired or wireless fashion. As with other embodiments, the information gathered or analyzed by sensor modules or sensors 304, 305, 26, and/or 25 can also be communicated to the central communication and control module 34 via a communication network such as the SCADA communication and control module 30 and via the network 34. The means of communication are not limited to SCADA and any other suitable communication network or protocol can be used as appropriate within a given environment. Note that in instances where a network is configured for a submersible environment, a wired connection and antenna that will reside and be configured above a given water level or flood zone may be desired for more robust wireless communications to a central communication and control (when wireless is used).

In yet another embodiment and referring to a system 400 of FIG. 4 similar to the system 300 of FIG. 3, at least one or more sensor modules 404 in a side or peripheal portion of the transformer tank 16 accesses the tank headspace where gases reside within a sealed tank. The system 400 in this embodiment would include a cap 402 without the sensor 404 since the sensor is coupled to or formed as part of the transformer tank 16 itself in a top portion of the tank where the headspace would typically reside (but not the cap in this instance). The sensor module 404 can include or be part of a combination sensor module 405 or part of the sensor 26 having one or more of the hydrogen sensor 21, moisture sensor 22, pressure sensor 23, temperature sensor 29, or the total combustible gas sensor 27 as in system 300 of FIG. 3. The combination sensor module 405 or sensor 26 can further include microprocessor 28 and optionally the dissolved gas analyzer 25 as illustrated. The sensor module 404 can be monitored and communicate data with the combination sensor module 405 or the sensor 26 in a wired or wireless fashion. As with other embodiments, the information monitored, or gathered or analyzed by sensor modules or sensors 404, 405, 26, and/or 25 can also be communicated to the central communication and control module 34 via the SCADA communication and control module 30 and via the network 34.

The embodiments 10, 200, 300, or 400 of FIGS. 1-4 can each include a power transformer cap configured to close and seal a top end of a power transformer tank that holds oil and to form a headspace containing combustible gas between the power transformer cap and the oil when the power transformer cap seals the top end of the power transformer tank. The embodiments herein are also applicable to other transformers or transformer tanks that form a headspace having gases. The systems (10, 200, 300, or 400) can further include at least one combustible gas sensor formed in the power transformer cap or an upper portion of the power transformer tank where the at least one combustible gas sensor is configured to measure an amount of combustible gas in the headspace and where the at least one gas sensor provides gas chromatography. In some embodiments, the at least one combustible sensor measures a combination of hydrocarbons that can include at least one among hydrogen gas, methane, acetylene, and/or carbon monoxide. In some embodiments the at least one combustible gas sensor is formed on a top side of the power transformer cap while in other embodiments the combustible gas sensor can be formed on a peripheral side of the power transformer cap. In other embodiments, the at least one combustible gas sensor is formed on a top peripheral portion of the power transformer tank that forms the headspace. In some embodiments, the power transformer tank is a submersible tank configured to be placed or at least be operable under the ground or below a given water level. In some embodiments, the system further includes a temperature sensor or a temperature sensor combined with the at least one combustible gas sensor. In some embodiments, the at least one combustible gas sensor is configured to estimate total dissolved combustible gases. In some embodiments, the system can include a dissolved gas analyzer coupled to the at least one combustible gas sensor where the dissolved gas analyzer can be contained within a housing for the at least one combustible gas sensor or provided separately.

In practical terms, the embodiment of FIG. 2 (most likely without the DGA 25) would be best for retrofitting existing transformers that already exist underground. Although not impossible, retrofitting sensors towards the bottom of a tank can be cumbersome and difficult in many scenarios. Even accessing a drain valve 18 in many instances in an existing underground or submersed transformer can be a challenge. Therefore, a sensor module 12 having access to a top portion of a transformer tank 16 (such as the top of the cap 14) would provide much easier access not only to monitor a new combination of parameters resulting from dissolved gases and/or moisture forming in the headspace, but also to enable the easy retrofitting of an existing transformer that would not have such monitoring equipment. Further note, with the appropriate communications, the monitoring can be done on a live and active transformer and such transformer would not need to be shut down or disabled to take such measurements. In other words, the embodiments herein enable easy access to a unique combination of parameters for live or online monitoring of the health conditions of a transformer. Furthermore, the structure and arrangement of the embodiments enables the easy access to allow retrofitting of transformers to include such monitoring equipment even under conditions where the transformers are underground or submersed. In such instances, the chamber in which the sensors resides should be water proof and adequately sealed to withstand being under water for long periods of time. For example, the chamber should be designed and configured to reside at least 25 feet below a water level and be able to remain under such conditions for at least 7 days. The chamber can be hermetically sealed in some embodiments.

In some embodiments, the system can further include a computer-storage media coupled to a processor and computer-executable instructions embodied in the computer-storage media that, when executed by one or more computing devices, perform a method that perform any number of steps such as analyzing a combination of parameters of hydrogen, moisture, and temperature to evaluate a health condition of the transformer, or measure an amount of combustible gas in the headspace, provide gas chromatography, or generate an alarm signal when a combination of input signals exceed one or more predetermined thresholds. Such predetermined thresholds can indicate certain levels of degradation of the power transformer or a need for maintenance.

Figure 5:
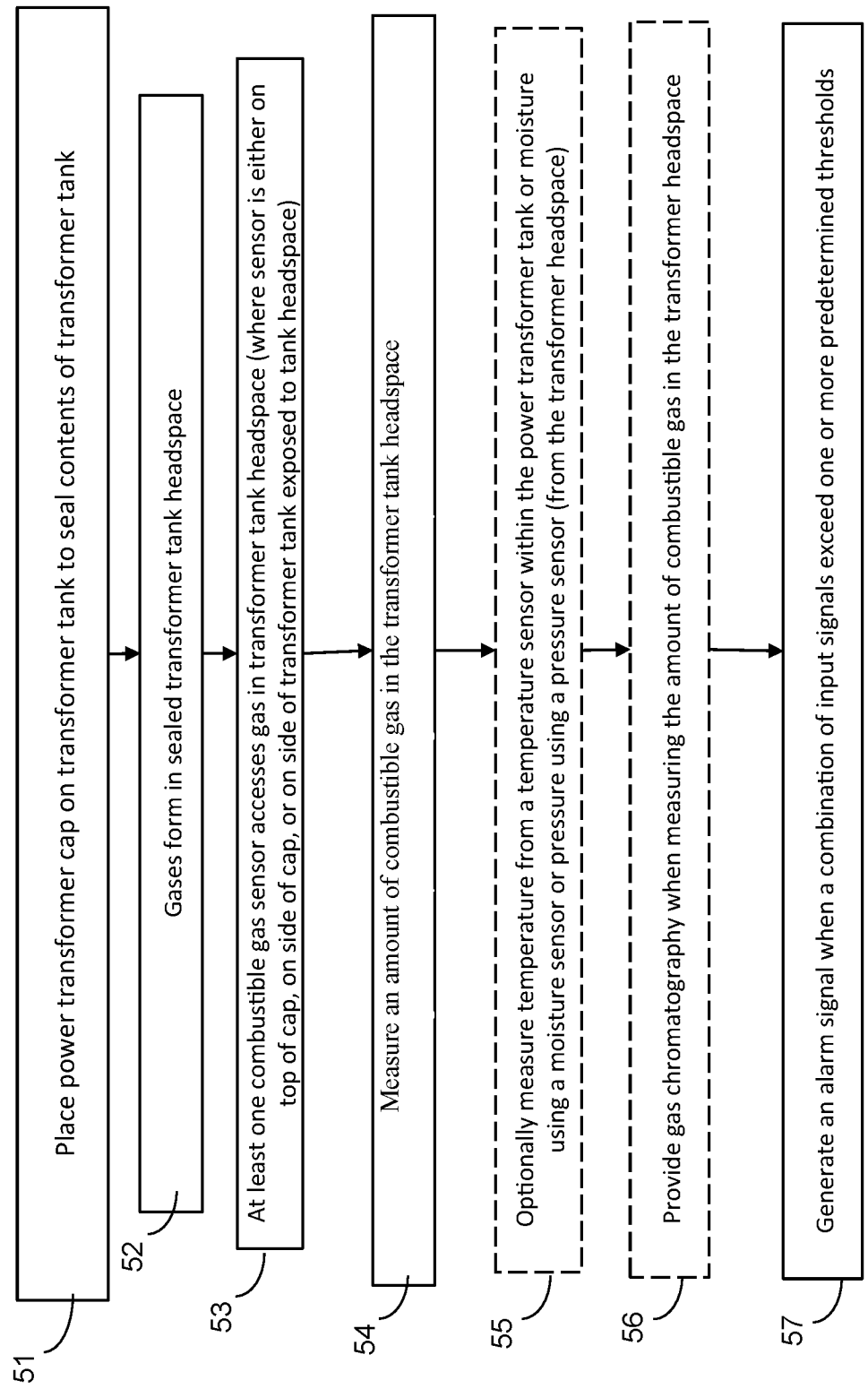
FIG. 5 is a flow chart of a monitoring method in accordance with an embodiment.

Referring to a flow chart illustrating a method 50 in FIG. 5 in accordance with the embodiments, the method can include the steps 51 of placing a power transformer cap on a transformer tank to seal the contents of the transformer tank. Over time, gases form in the sealed transformer tank headspace at step 52. Analysis of the gases formed in the tank headspace can provide indicators of degradation or of a need for maintenance or repair. At 53, at least one combustible gas sensor accesses gas in the transformer tank headspace where the sensor can be either on a top portion of a cap, on a side portion of the cap, or on a upper side or peripheral portion of the transformer tank that enables access to gases in the tank headspace. The combustible gas sensor used at 53 can be merely a hydrogen gas sensor or can be a combination of a hydrogen gas sensor and a total combustible gas sensor. At 54, the method 50 can measure and/or monitor an amount of combustible gas in the transformer tank headspace. The measurements made of the gases in the headspace should have a corresponding proportionality to the gases that might typically be measured from gases sampled from dissolved gases in oil from the power transformer tank. This corresponding proportionality can provide the appropriate indications as to when the transformer tank has degraded to the extent replacement, maintenance or repair is required. Note that this can be done without necessarily having to access oil at a drain of the transformer tank. In some embodiments, the method can further include the step 55 of measuring temperature from a temperature sensor within the power transformer tank or measuring pressure from a pressure sensor within the power transformer tank or moisture from a moisture sensor within the power transformer tank. Again, these sensors are accessing and sensing or monitoring the parameters of hydrogen, or total combustible gases, or temperature, or pressure, or moisture from a transformer headspace and not from a drain, which would typically reside at the bottom of a transformer tank. As noted previously, access to a drain, particularly a drain already in the field and even more so when submersed would be difficult to access. At step 56, the method can optionally include providing gas chromatography when measuring the amount of combustible gas in the transformer headspace. At step 57, the method can generate an alarm when a combination of input signals exceeds one or more predetermined thresholds as discussed above. The method 50 can further bring the transformer offline if the combination of input signals is above yet another higher predetermined threshold.

Referring back again to FIG. 1, the main technical features of one embodiment of a monitoring system or sensor 20 when a sensor is optionally used at a drain valve can be embodied by the use of one complex sensor through which all the necessary parameters of the transformer are monitored and controlled. The complex sensor of the monitoring system 20 can be located inside the transformer tank and more particularly all within or at least partially within the drain valve 18 of the transformer tank. Such ideal location can provide protection from external electromagnetic interference. Structurally, the design and dimensions of the integrated sensor is configured to be easily mounted on the transformer main valve which can be typically be a ball valve or gate valve.

The effective microprocessor used for the monitoring system can be so compact that it can be completely placed on the output part of the sensor, forming a single whole unit as part of the monitoring system coupled to the transformer main valve.

Operationally, information from the system can be transferred to a supervisory control and data acquisition (SCADA) control system on an industrial RS-485 interface or other appropriate interface. To implement the functions of diagnostic monitoring of power transformers with the proprietary system herein, an "iNVA" software is supplied, equipped with a powerful diagnostic and expert core. The software can algorithmically make an integrated approach to monitoring of power transformers in a manner that provides high economic efficiency in a compact technical solution that further provides ease of installation.

Each of the three or more diagnostic methods implemented in the system 20 (when used) makes it possible to effectively evaluate the state of the main subsystems of the power transformer. In one aspect, the system 20 monitors or measures partial discharges in the tank of the transformer. Measurement of partial discharges in the transformer tank allows timely detection of problems in transformer insulation and, in comparison with the conventional control system for dissolved gases in oil, responds more quickly to the occurrence of defects. The built-in partial discharge registration system (PD) also monitors the insulation status of high-voltage bushings, which is very important due to the wide introduction of hard-insulated bushings, in which the appearance of PD even a small level is an important diagnostic sign of defects. The measurement of partial discharges in the tank of the transformer by the system 20 can be performed in the ultrahigh-frequency (UHF) band, which captures frequencies from 0.5 to 1.5 GHz. This makes it possible to exclude the influence of relatively low-frequency corona discharges and to use the transformer tank as an effective screen (similar to a Faraday cage) against external electromagnetic interference. Optionally, the system can also implement a dissolved gas analysis (DGA) system as well, but only as a further enhancement. The DGA 25 shown is external to the sensor 20, but if sufficiently designed and configured to be small enough, the DGA 25 can also be arranged and constructed to be formed within the sensor 20 in some embodiments.

The system 20 (when used separately from the sensor 26 or in combination with) can further monitor or measure the moisture in the oil. The monitoring system for moisture content in oil is designed to detect the presence of a dispersed phase of water in the oil of the transformer tank, to determine its concentration. Water in this phase can have a catastrophic effect on the electrical strength of the oil. For the convenience of operation of the transformer in the system herein, an adaptive mathematical model is implemented that describes the process of transition of the dispersed phase of moisture in the oil into the solid insulation of the transformer and back when the temperature of the tank changes. This model is especially useful for determining the permissible modes of operation of a transformer under conditions of varying loads and negative external temperatures. Used in combination to measure the moisture in the headspace 11A and 11B using sensor 22, the moisture models indicative of degradation can be further refined with the additional data gathered. The system 20 can also monitor oil temperature. The oil temperature in the transformer tank is an important operational parameter of the transformer. The current value of the tank temperature is used by the monitoring system not only for evaluating the operating modes of the transformer, but also for use in various built-in diagnostic models and algorithms of the expert system. As with other parameters, the temperature measured within the system 20 at the drain valve can certainly be combined and considered with temperature measured with temperature sensor 29 that measures the temperature within the headspace of the transformer tank in order to make appropriate assessments of transformer health.

The system 20 can further include sensors for measuring hydrogen as a component of transformer oil. For clarification, please note that the system 20 can operate independent of the sensor module 12 and the sensor module 12 can operate independent of the system 20 in the various embodiments of the present invention.

In one typical configuration according some of the embodiments, the system can have the following specifications (but is not limited to such specification in all embodiments):

| Technical data | |
|---|---|
| Supply voltage: | 85 . . . 264 V AC/47 . . . 63 Hz |
| | 120 . . . 370 V DC |
| | 95 . . . 370 V DC (optional) |
| Power consumption: | max. 20 VA |
| Dimensions: | W 25" × H 6½" × D 10 |
| Weight: | approx. 20 lb |
| Operation temperature: | −40° C. . . . +55° C. |
| Storage temperature: | −20° C. . . . +65° C. |
| Operating Pressure at Analyzer: | 5 Bar (72 Psi) |
| Adapter Fitting: | 1½ NPT |
| Sensor length, (on request) | 16" |
| Partial discharge registration system | |
| Range of partial discharges: | 0.5 . . . 1.5 GHz |
| Range of amplitudes of PD signals: | −70 . . . −10 dBm |

| Technical data -continued | |
|---|---|
| Moisture control in Oil | |
| Relative moisture | 0 . . . 100% |
| Accuracy of determination of moisture | ±2.0% |
| Tank temperature control | |
| Range of measured temperatures | −40 . . . +125° C. |
| Accuracy of temperature measurement | ±0.3% |
| H2 Sensor | |
| Measurement Range (H2) | 25-5000 ppm |
| Accuracy (H2) | 20% of reading or 25 ppm, whichever is greater |
| Repeatability (H2) | 10% of reading or 15 ppm, whichever is greater |
| Response Time (H2) | <90 min (90% of step change) |
| Resolution of measurement in oil | 1 ppm |
| Detection limit | 25 ppm |
| Max Limit (H2) | 5,000 ppm |
| The cross-sensitivity to other gases (CO, CO2, CH4, C2H2, C2H4, C2H6, C3H8, etc.) | Shall be below 2% |
| Operating Temperature of Oil | −20° C. . . . 85° C. |
| Initial Start-up time | 2 hours, 12 hours for full specification |
| Communication | |
| Communication interfaces | RS-485 MODBUS RTU |

Again, note that whether a sensor or combination sensor 20 is used with the drain valve 18 is independent of the concept of using a sensor for measuring combustible gases and other parameters in the headspace of the transformer tank. No prior existing transformer system includes a sensor that measures a combination of combustible gases in the headspace of the transformer tank using a embedded sensor in the transformer tank cap on either a top portion of the transformer tank cap or a side or peripheral portion of the transformer tank cap in combination with other measured parameters. Alternatively within the embodiments, the sensor can be formed or placed on a top portion of the transformer tank itself instead of the transformer cap as long as the sensor has access to the gases formed in the tank headspace. Among the benefits of having the sensor in the cap of the transformer tank include easier access to the sensor when place on the top portion of the transformer tank or cap. Furthermore, when trying to retrofit older transformers that may not have such sensors or that have sensors that access a drain valve toward a bottom portion of the transformer tank, the embodiments herein enable easy retrofitting by replacing a plain cap of the old transformer with a cap having the sensor as disclosed herein.

Various embodiments of the present disclosure can be implemented on an information processing system. The information processing system is capable of implementing and/or performing any of the functionality set forth above. Any suitably configured processing system can be used as the information processing system in embodiments of the present disclosure. The information processing system is operational with numerous other general purpose or special purpose computing system environments, networks, or configurations. Examples of well-known computing systems, environments, and/or configurations that may be suitable for use with the information processing system include, but are not limited to, personal computer systems, server computer systems, thin clients, hand-held or laptop devices, multiprocessor systems, mobile devices, microprocessor-based systems, set top boxes, programmable consumer electronics, network PCs, minicomputer systems, mainframe computer systems, Internet-enabled television, and distributed cloud computing environments that include any of the above systems or devices, and the like.

For example, a user with a mobile device may be in communication with a server configured to implement the monitoring system using the aforementioned sensors, according to an embodiment of the present disclosure. The mobile device can be, for example, a multi-modal wireless communication device, such as a "smart" phone, configured to store and execute mobile device applications ("apps"). Such a wireless communication device communicates with a wireless voice or data network using suitable wireless communications protocols. Alternatively, the monitoring system can be a computing and monitoring system with or without wireless communications as the case may be.

The monitoring system may include, inter alia, various hardware components such as processing circuitry executing modules that may be described in the general context of computer system-executable instructions, such as program modules, being executed by the system. Generally, program modules can include routines, programs, objects, components, logic, data structures, and so on that perform particular tasks or implement particular abstract data types. The modules may be practiced in various computing environments such as conventional and distributed cloud computing environments where tasks are performed by remote processing devices that are linked through a communications network. In a distributed cloud computing environment, program modules may be located in both local and remote computer system storage media including memory storage devices. Program modules generally carry out the functions and/or methodologies of embodiments of the present disclosure, as described above.

In some embodiments, a system includes at least one memory and at least one processor of a computer system communicatively coupled to the at least one memory. The at least one processor can be configured to perform a method including methods described above.

According yet to another embodiment of the present disclosure, a computer readable storage medium comprises computer instructions which, responsive to being executed by one or more processors, cause the one or more processors to perform operations as described in the methods or systems above or elsewhere herein.

As shown in FIG. 6, an information processing system 101 of a system 600 can be communicatively coupled with the data analysis module 150 and a group of client or other devices, or coupled to a presentation device for display at any location at a terminal or server location. According to this example, at least one processor 102, responsive to executing instructions 107, performs operations to communicate with the data analysis module 150 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the data analysis module 150 and more generally used by the information processing system 600. The data analysis module 150 can be coupled to one or more sensors 152 that measures the various parameters previously described that are indicative of transformer health (including, but not limited to hydrogen, total combustible gas, moisture, temperature, pressure, partial discharge, etc.) Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The data analysis module 150, and the information processing system 600, can use the information from the history log such as in the analysis process and in making decisions related to determining whether data measured is considered within or outside of a threshold indicative of a healthy transformer.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 600 includes a user interface 110 that comprises a user output interface 112 and user input interface 114. Examples of elements of the user output interface 112 can include a display, a speaker, one or more indicator lights, one or more transducers that generate audible indicators, and a haptic signal generator. Examples of elements of the user input interface 114 can include a keyboard, a keypad, a mouse, a track pad, a touch pad, a microphone that receives audio signals, a camera, a video camera, or a scanner that scans images. The received audio signals or scanned images, for example, can be converted to electronic digital representation and stored in memory, and optionally can be used with corresponding voice or image recognition software executed by the processor 102 to receive user input data and commands, or to receive test data for example.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

FIGS. 1-5 illustrate examples of systems, methods or process flows, according to various embodiments of the present disclosure, which can operate in conjunction with the information processing system 600 of FIG. 6.

What is claimed is:

1. A sensor module for monitoring a headspace of a transformer having insulating material, comprising:
    a chamber configured for coupling and accessing gasses from the headspace of the transformer that is above a liquid level of the insulating material in the transformer, wherein the chamber of the sensor module forms a sealed chamber when coupled with the headspace of the transformer;
    a plurality of sensors within the chamber of the sensor module that directly accesses gasses in the headspace above the liquid level of the transformer via an aperture in a power transformer tank cap, the plurality of sensors comprising a hydrogen sensor for detection of hydrogen in the headspace, of a total combustible gas sensor for detection of total combustible gases, a moisture sensor for detection of moisture content in the insulating material in the transformer, a pressure sensor, and a temperature sensor; and
    one or more processors coupled to the plurality of sensors, wherein the one or more processors are configured to generate an alarm signal when a combination of the hydrogen sensor and the total combustible gas sensor exceed a predetermined threshold based on a combination of measurements of gases from the hydrogen sensor and the total combustible gas sensor having a corresponding proportionality in measurements to gas levels typically measured from gases sampled from dissolved gases in oil indicative of a transformer in a degraded state to the extent needing replacement, maintenance or repair.

2. The sensor module of claim 1, wherein the sealed chamber is configured for coupling and accessing gasses from the headspace of the transformer via a peripheral side of the power transformer tank cap.

3. The sensor module of claim 1, wherein sensor module further contains a dissolved gas analyzer.

4. The sensor module of claim 1, wherein the sensor module further comprises a transmitter coupled to the processor for transmitting measurements from the hydrogen sensor and a second sensor among the total combustible gas sensor, the moisture sensor, the pressure sensor, or the temperature sensor or for transmitting the alarm signal to a receiver.

5. The sensor module of claim 1, wherein the sensor module is arranged and constructed to withstand water pressure up to depths of 25 feet or less.

6. The sensor module of claim 1, wherein the total combustible gas sensor measures a combination of hydrocarbons comprising at least one among hydrogen gas, methane, acetylene, and carbon monoxide.

7. The sensor module of claim 1, wherein the sensor module is formed on a top side or a peripheral side of the power transformer tank cap that seals the transformer and forms the headspace.

8. The sensor module of claim 1, wherein the transformer comprises a submersible tank configured to be placed under the ground and the sensor module is configured to operate with the submersible tank.

9. The sensor module of claim 1, wherein the sensor module is coupled to a dissolved gas analyzer.

10. The sensor module of claim 1, wherein the sensor module comprises the hydrogen sensor, the total combustible gas sensor, the moisture sensor, the pressure sensor, and the temperature sensor all within a chamber that is sealed from an external environment when the sensor module directly couples to the headspace of the transformer.

11. The sensor module of claim 1, wherein the system further comprises a computer-storage media coupled to one or more processors and computer-executable instructions embodied in the computer-storage media that, when executed by one or more processors, perform a method comprising:
    analyzing a combination of parameters of hydrogen and one or more of moisture, pressure, and temperature to evaluate a health condition of the transformer.

12. A system, comprising:
    a transformer cap configured to close and seal a top end of a transformer tank that holds oil and to form a headspace above a liquid portion of the oil and containing combustible gas between the transformer cap and the oil when the transformer cap seals the top end of the transformer tank; and
    a sensor module in a chamber of the sensor module configured for coupling and accessing gasses from the headspace of the transformer via the transformer cap, wherein the chamber is sealed from an external environment when sensor module directly couples to the headspace of the transformer to form a sealed chamber;
    a plurality of sensors placed within the chamber of the sensor module and the sensor module being in direct communication with gasses above the liquid portion of the oil in the headspace of the transformer, the plurality of sensors comprising a hydrogen sensor and a total combustible gas sensor and at least a third sensor, and a fourth sensor selected from the group consisting of, a moisture sensor, a pressure sensor, and a temperature sensor; and
    one or more processors coupled to the plurality of sensors, wherein the processors are configured to generate an alarm signal when a combination of the hydrogen sensor and the total combustible gas sensor exceed a predetermined threshold based on a combination of measurements of gases from the hydrogen sensor and the total combustible gas sensor having a corresponding proportionality in measurements to gas levels measured from gases sampled from dissolved gases in oil indicative of a transformer in a degraded state to the extent needing replacement, maintenance or repair.

13. The system of claim 12, wherein at least one combustible gas sensor formed in the power transformer cap or an upper portion of the power transformer tank, wherein the at least one combustible gas sensor is configured to measure an amount of combustible gas in the headspace and wherein the at least one gas sensor provides gas chromatography.

14. The system of claim 12, wherein the sensor module is formed on a top side of the transformer cap.

15. The system of claim 12, wherein the sensor module is formed on a top peripheral portion of the transformer tank that forms the headspace.

16. The system of claim 12, wherein the transformer tank is a submersible tank configured to be placed under the ground.

17. The system of claim 12, wherein the plurality of sensors comprises a fifth sensor selected among the hydrogen sensor, the total combustible gas sensor, the moisture sensor, the pressure sensor, and the temperature sensor.

18. The system of claim 12, wherein the total combustible gas sensor is configured to estimate total dissolved combustion gases.

19. A sensor module for monitoring a headspace of a submersible transformer having insulating material, comprising:

a chamber configured for coupling and accessing gasses from the headspace of the submersible transformer, wherein the headspace is above a liquid level of the insulating material in the submersible transformer;

a plurality of sensors placed within the chamber of the sensor module that directly accesses gasses in the headspace formed above the liquid level of the insulating material of the sealed chamber to form a sealed chamber upon coupling between the chamber of the sensor module and the headspace, the plurality of sensors comprising a hydrogen sensor and a total combustible gas sensor and at least a third sensor, and a fourth sensor selected from the group consisting of, a moisture sensor, a pressure sensor, and a temperature sensor; and one or more processors coupled to the plurality of sensors wherein the one or more processors are configured to generate an alarm signal when a combination of the hydrogen sensor and the total combustible gas sensor sensor exceed a predetermined threshold based on a combination of measurements of gases from the hydrogen sensor and the total combustible gas sensor having a corresponding proportionality in measurements to gas levels measured from gases sampled from dissolved gases in oil indicative of a transformer in a degraded state to the extent needing replacement, maintenance or repair.

20. The sensor module of claim 19, wherein the one or more processors are configured to generate an alarm signal when a combination of the hydrogen sensor, the total combustible gas sensor and at least two among the moisture sensor, the pressure sensor, or the temperature sensor exceed a number of predetermined thresholds.

* * * * *